United States Patent [19]

Bertelli

[11] Patent Number: 4,654,373

[45] Date of Patent: Mar. 31, 1987

[54] PHARMACEUTICAL FORMULATIONS CONTAINING COENZYME $Q_{10}$ SUITABLE FOR TOPIC ADMINISTRATION

[75] Inventor: Alberto Bertelli, Milan, Italy

[73] Assignee: Italfarmaco S.A., Lugano, Switzerland

[21] Appl. No.: 711,034

[22] Filed: Mar. 12, 1985

Related U.S. Application Data

[63] Continuation-in-part of Ser. No. 476,556, Mar. 18, 1983, abandoned.

[30] Foreign Application Priority Data

Mar. 19, 1982 [IT] Italy ............................... 20274 A/82

[51] Int. Cl.$^4$ ............................................. A61K 31/12
[52] U.S. Cl. ................................................... 514/690
[58] Field of Search ........................................ 514/690

[56] References Cited

PUBLICATIONS

Chemical Abstracts, vol. 97 (1982) #61038t; Sangyo.
Chemical Abstracts, vol. 100 (1984) #145017d; Eisai Co. Ltd.
Chemical Abstracts, vol. 99 (1983) #164038p; Seuref.
Chemical Abstracts, vol. 100 (1984) #39458p; Shiseido Co. Ltd. et al.
Chemical Abstracts; vol. 84 (1976) #146509d; Albert et al.
Chemical Abstracts; vol. 94 (1981) #90365r; Tokai.
Chemical Abstracts; vol. 92 (1980) #176159x; Degli et al.
Chemical Abstracts; vol. 97 (1982) #28598c; Sangyo.
Chemical Abstracts; vol. 97 (1982) #78891p; Nippon.

Primary Examiner—Leonard Schenkman
Assistant Examiner—Joseph A. Lipovsky
Attorney, Agent, or Firm—Walter H. Schneider

[57] ABSTRACT

The present invention refers to new pharmaceutical compositions which contain Coenzyme $Q_{10}$ in amounts from 0.0001 to 10%, dissolved or suspended in a suitable vehicle and which are useful in the pharmaceutical and cosmetological field for the topical cutaneous treatment of skin diseases and for the prophylaxis of dystrophias or dysmetabolic conditions of the cutis.

5 Claims, No Drawings

PHARMACEUTICAL FORMULATIONS CONTAINING COENZYME $Q_{10}$ SUITABLE FOR TOPIC ADMINISTRATION

This application is a continuation-in-part of application Ser. No. 476,556 filed Mar. 18, 1983, now abandoned.

The present invention refers to new pharmaceutical compositions containing Coenzyme $Q_{10}$. The compositions of the invention also contain suitable, pharmaceutically acceptable carriers. The pharmaceutical compositions of the invention are provided for the topical use and for the treatment of diseases of skin and mucous membranes and for the prevention of dystrophic or dysmetabolic conditions of the cutis and its annexes.

Coenzyme $Q_{10}$ has the following structural formula (I)

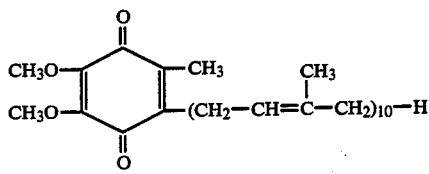

and its chemical name is 2,3-dimethoxy-5-methyl-6-decaprenyl-benzoquinone.

The activity of Coenzyme $Q_{10}$ is strictly connected with the tissular respiratory processes.

A wide bibliography pointed out its ability to solve or prevent anoxic tissular damages, particularly in the myocardium.

Other positive effects have been obtained by means of Coenzyme $Q_{10}$ in the treatment of arterial hypertension, of muscular dystropy, of periodontopathies, of penfigus and of lichen planus.

In all such pathological conditions, it was also noticed that the administration of Coenzyme $Q_{10}$ led to a normalization of tissular concentrations of this enzyme, otherwise scarce.

In spite of the fact that the therapeutic action of Coenzyme $Q_{10}$ is clearly evident in inflammed and impaired tissues such as gingival mucous membranes, in the periodontopathies, or in the penfigus or lichen planus, its therapeutic use has been carried out up to now only by the oral or parenteral administration route.

However, such administration routes generally do not give the desired effects. There is an increasing need for pharmaceutical compositions containing Coenzyme $Q_{10}$ which allow to obtain plasmatic and tissutal concentrations sufficient to exert a therapeutic effect.

Although the effective concentrations displaying an effective action at cellular and tissutal levels are very low, the oral and parenteral administration of Coenzyme $Q_{10}$ makes it possible to remedy to the enzymatic system deficiencies which are responsible for a variety of diseases.

This fact has been proved by precise dosage methods of Coenzyme $Q_{10}$ by means of HPLC (Kouichi Abe et al.—Proc. Int. Symposium "Biomedical and Clinical Aspects of $Co_{10}$", Austin, Jan. 1981—Esevier/North Holland—Y. Yamamura et coll. Ed.).

Such a method proved the difficulty in changing the Coenzyme $Q_{10}$ endogen concentration by oral administration of this compound.

Efforts have been made to overcome the above mentioned drawback, by increasing the Coenzyme $Q_{10}$ oral dosages from 5-10 mg/dosage (15-30 mg pro die) to 50-100 mg/dosage (100-200 mg pro die), i.e. ten times higher values.

The administration of such high dosages gives satisfactory clinical results (Hamada M. et al.—Fourth Int. Sym. on the Biomedical and Clinical Aspects of Coenzyme Q—Max Planck Institute—Martinsried, München, Germany 11-6-1983; Folkersk. et al.—Drugs Expt. Clin. Res., 10-513-1984), but it increases, sometimes intolerably, the side-effects of the drug.

It should be pointed out that such favourable effects relate to metabolically very active organs, such as liver, heart and lung. In the peripheral tissues which are metabolically less active no changes in Coenzyme $Q_{10}$ are detectable even after oral administration of high doses of the drug.

Recently, the parenteral route has been used to obtain higher tissutal concentrations of Coenzyme $Q_{10}$. However, this technique is scarcely advantageous, due to the very low solubility of Coenzyme $Q_{10}$ in excipients compatible with its parenteral administration.

It is therefore evident that oral administration of Coenzyme $Q_{10}$ can be used only in the treatment of diseases affecting metabolically very active organs, whereas Coenzyme $Q_{10}$, if administered orally, proves to be substantially ineffective at the cutaneous level.

Therefore, a pressing need there was for pharmaceutical compositions allowing to advantageously perform a local therapy of the above mentioned diseases or of other pathological or privation derived conditions. It has now been surprisingly found, that the pharmaceutical compositions according to the present invention allow to effectively increase the concentration of Coenzyme $Q_{10}$ directly in impaired or damaged tissues.

Accordingly, the pharmaceutical compositions of the invention are also useful for the local application of Coenzyme $Q_{10}$ on the cutis in cases of metabolic respiratory impairments of the cutis, caused by chemical or physical treatments (heat, cold, U.V. rays) or simply by a slowing of cutaneous respiratory processes connected, for examples, with age and wear.

The pharmaceutical compositions for topical application of the present invention can be prepared by dissolving or suspending Coenzyme $Q_{10}$ in vegetal oils such as seed oil or soy-bean oil, lecithine, glycerol, glycerylfurfurole, Tween 80 or other derivatives, suspending agents or diluents.

After the addition of suitable carriers and formulation aids to such solutions or suspensions, the compositions of the present invention can be formulated as pastes, creams, ointments, gels, lotions, unguents.

The pharmaceutical compositions according to the present invention contain Coenzyme $Q_{10}$ as the active principle, in amounts from 0.1 to 10%, preferably from 0.25 to 1%. The new pharmaceutical compositions can also be used for cosmethological purposes. In such a case, the content of Coenzyme $Q_{10}$ can be lower than the limits previously mentioned, being preferably from 0.0001 to 0.1%.

The pharmaceutical or cosmethological compositions according to the present invention may also contain other topically active components beside the active principle (Coenzyme $Q_{10}$).

The pharmaceutical compositions according to the present invention represent a valuable therapeutic enrichment since they allow to successfully treat the previously cited diseases, and to solve same dermatological problems which cannot be faced with oral administration.

Moreover, the compositions according to the invention lack any toxicity and are well accepted by patients owing to the simplicity of their use.

Moreover, the topical use allows a more immediate effect which is localized to the ill region, thereby reducing the side effects which could be produced by the unnecessary oral or parenteral administration of Coenzyme $Q_{10}$.

The toxicity, theratogenesis, cutaneous absorption and pharmacological tests hereinafter described have been performed by using pharmaceutical compositions according to the invention containing Coenzyme $Q_{10}$ (at the concentrations specified) in a vehicle of soy-bean oil, lecithine or peanut oil.

ACUTE TOXICITY TESTS

The low toxicity of Coenzyme $Q_{10}$ administered at high doses both by oral and by subcutaneous or intraperitoneal route has been already shown (the $LD_{50}$ of the product turned out in fact to be higher than 4 g/kg by the oral route and 250–500 mg/kg by the subcutaneous or intraperitoneal routes). To assess the toxicity of the product administered by the topical cutaneous route, two groups of forty Wistar rats of both sexes in the same number, carefully depilated on the back, were used.

To a group of these rats, the depilated skin was also abraded. On the cutis so prepared after two days the compositions of the invention containing increasing amounts of Coenzyme $Q_{10}$ in the ratio of 5 mg up to 20 mg for each square centimeter of depilated skin, were spread for each group of ten rats.

The immediate observation as well as the one carried out eight days after the treatment did not show the appearance of any mortality cases, toxic effect or intolerance in the so treated rats.

Similar experiences were carried out also on a group of 8 New Zealand rabbits of both sexes, having the back depilated. The cutis of 4 of these animals was also abraded.

Two days after the depilation, the compositions of the invention, corresponding to doses of Coenzyme $Q_{10}$ ranging from 5 to 20 mg per square centimeter of area of the depilated back, were spread on the cutis of the animals so prepared.

Also in this case, neither immediately after the administration nor after 8 days, mortality cases or clear toxicity were noticed.

CHRONIC TOXICITY TESTS

These tests were carried out by administering locally on the skin of two groups of 30 male Wistar rats and of 6 male New Zealand rabbits with the skin epilated, the skin of one group being epilated and abraded, a pharmaceutical composition for a total amount of 50 mg/kg/die of Coenzyme $Q_{10}$.

The administration went on daily for 60 consecutive days.

Before the start of the treatment and at the end all the animals were subjected to a series of controls and examinations regarding the ponderal increase, red-cells and white cells count, haemoglobin concentration in the blood, glycemia, azotemia, transaminases and blood total proteins. The urinary elimination was also tested. At the end of treatment all the animals were killed and accurate anatomopathological and histopathological examinations were performed on each animal with particular regard to the zones of treated skin.

All the exams performed did not show, in comparison with the untreated control animals, any significative difference in the different biological parameters considered. Also the histological examinations of the skin of the treated animals did not show any pathological change.

THERATOGENESIS TEST

In order to evaluate if the administration by the topical route of Coenzyme $Q_{10}$ could interfere on the normal ebryonal or phaetal development, a pharmaceutical composition of the invention corresponding to an amount of Coenzyme $Q_{10}$ of 50 mg/kg/die was spread on the epilated and abraded skin of ten pregnant Wistar rats.

The administration was carried out from the seventh to the fifteenth day of pregnancy.

On the 21st day from the start of pregnancy, the phoetuses were removed, from all the treated and control rats, counted and morphologically observed. The main internal organs were also subjected to observation.

Under such experimental conditions, no alteration or malformation was noticed.

TEST OF CUTANEOUS ABSORPTION OF COENZYME $Q_{10}$

Experiences in the Rat

In order to evaluate the cutaneous absorption of Coenzyme $Q_{10}$ after its application on the skin a group of male Wistar rats of the average weight of 280 g was used. The animals were epilated on the back and a composition corresponding to a dose of Coenzyme $Q_{10}$ of 5 mg/kg/cm$^2$ of skin was applied on the epilated back.

Samples of skin were then removed both from treated and untreated animals at intervals of 1, 3, 6 and 24 hours from treatment. The skin, together with the removed subcutaneous tissue, was homogenized and kept at $-20°$ C. till the moment of analysis.

Samples of 5 g each of tissue were saponified in the presence of pyrogallole.

The fraction containing Coenzyme $Q_{10}$ and other neutral fats was extracted with hydrocarbon solvents and purified chromatographically on column.

The spectrophotometric measurement was performed according to the method described by Linn B. O., Page A. C., Wong E. L., Gale, P. H., Shunk C. H., Folkers K. [J. Am. Chem. Soc., 81, 4007 (1959)].

The results obtained by this method did not show the presence of measurable amounts of Coenzyme $Q_{10}$ in the normal cutaneous tissue.

The Coenzyme $Q_{10}$ was found on the contrary in the samples of tissue on which the Coenzyme $Q_{10}$ had been previously applied. The amounts found were in relation with the administered dose and ranged from 0.2 $\mu$g/100 g of tissue to 17 $\mu$g/100 g of tissue. The highest concentrations were found from the third to the sixth hour after the administration.

EXPERIMENTS IN VOLUNTEERS

For these tests the method described by Tauber and al. [Arzneimittel Forschung, 26, N7b, 1492 (1976)].

On 4 health volunteers, areas of about 30 cm$^2$ of skin whose corneous layer had been removed, were spread with a composition corresponding to 1 mg/cm$^2$ of Coenzyme $Q_{10}$.

Immediately after the application and after 24 hours from the application on the skin, the composition not absorbed was removed by cotton-wool and the cotton-wool used for the removal was extracted with chloroform/ethanol.

After saponification in presence of pyrogallole the fraction containing Coenzyme $Q_{10}$ and other neutral fact was extracted with hydrocarbon solvents and purified chromatographically on column.

The spectrophotometric measure was carried out according to the method described by Linn and al. [J. Am. Chem. Soc., 81, 4007 (1959)].

The differences existing between the amount of substance administered and the amount of recovered substance showed a mean percent absorption of $18.5 \pm 6.2\%$.

TEST ON DISTRIBUTION AFTER ORAL, PARENTERAL AND TOPIC ADMINISTRATION

Oral Administration

Rats were treated with 50 mg/kg of Coenzyme $Q_{10}$ by oral route and the concentration of the active principle was determined by using the HPLC method in several organs after 30 min., 60 min. and 6 hours.

As shown in Table 1, after oral administration of Coenzyme $Q_{10}$ no appreciable appearance of cutaneous concentration of the product is noted.

The concentration changements are negligeable also at the plasmatic level, whereas substantial changes occur at the heart level. These facts should prove the rapid disappearance of the drug from the circulation after its administration, and the preferential concentration of the drug in metabolically active organs such as heart and kidney.

TABLE 1

Mean plasmatic (μg/ml) and tissutal (μg/g) concentrations of Coenzyme $Q_{10}$ in the rat, after oral treatment with 50 mg/kg oil Coenzyme $Q_{10}$, at different times after the administration.

|  | 30 min. | 60 min. | 6 hours |
| --- | --- | --- | --- |
| Plasma | 0.17 | 0.19 | 2.7 |
| Heart | 7.1 | 12.3 | 14.7 |
| Kidney | 6.5 | 10.1 | 15.6 |
| Liver | 4.1 | 7.1 | 9.8 |
| Cutis | — | — | — |

PARENTERAL ADMINISTRATION

Rats were treated with 20 mg/kg of Coenzyme $Q_{10}$ by intramuscular injection and the concentration of the active compound was determined by HPLC after 30 min., 60 min. and 6 hours.

The results are shown in Table 2. It is clearly seen that no concentration in the cutis is present at any time.

TABLE 2

Mean plasmatic (μg/ml) and tissutal (μg/g) concentrations of Coenzyme $Q_{10}$ in the rat, after intramuscular treatment with 20 mg/kg of Coenzyme $Q_{10}$, at different times after the administration.

|  | 30 min. | 60 min. | 6 hours |
| --- | --- | --- | --- |
| Plasma | 0.27 | 0.94 | 0.80 |
| Heart | 10.5 | 14.30 | 16.2 |
| Kidney | 9.5 | 11.5 | 10.2 |
| Liver | 11.7 | 12.6 | 14.4 |
| Cutis | — | — | — |

TOPIC ADMINISTRATION

Rats were cutaneously treated with 2 mg/cm$^2$ of skin of Coenzyme $Q_{10}$ and the concentration was measured by the HPLC method. The results are listed in Table 3 for two different vehicles.

The above Table clearly shows that the cutaneal topic administration of the product modifies the Coenzyme $Q_{10}$ concentration at the cutis level. A good increase is obtained by using vegetal oils as solvents and excipients.

TABLE 3

Cutaneous mean concentrations (μg/g) of Coenzyme $Q_{10}$ in the rat after topical administration of Coenzyme $Q_{10}$ (2 mg/cm$^2$ cutis).

|  | 30 min. | 60 min. | 6 hours |
| --- | --- | --- | --- |
| Coenzyme $Q_{10}$ in peanut oil | 5.5 | 8.2 | 7.5 |
| Coenzyme $Q_{10}$ in soy-bean oil | 4.6 | 6.4 | 5.2 |
| Coenzyme $Q_{10}$ in olive oil | 5.8 | 9.2 | 8.2 |

PHARMACOLOGICAL TESTS

Coenzyme $Q_{10}$ administered locally by topical route in the form of a composition of the invention proved to be effective in activating the tissular regenerative processes and to exert a significant healing action as well as to decrease the local damage caused by burns and to prevent the onset of dental caries.

Experiences performed by making holes of the same diameter in rabbits' ears of New Zealand strain and spreading locally the skin around the holes made in the ears with a composition of Coenzyme $Q_{10}$ at the concentration of 5 mg/cc, showed that the tissular regeneration and healing processes in the rabbits treated with Coenzyme $Q_{10}$ are much faster than in the not treated rabbits.

Experience performed in the hamster fed by cariogenic diet have also showed that the application with a suitable spatula on the dental gingival region of these animals of Coenzyme $Q_{10}$ in a dose per animals of 25 mg/kg, prevent the onset of dental caries in more than 50% of the treated animals. Some experiences performed on the experimental burn in the rat showed the protective effect exerted by Coenzyme $Q_{10}$ applied by topical route.

In male Wistar rats the preventive application of Coenzyme $Q_{10}$ on the epilated skin of the back of a composition corresponding to a dose of 1–2 mg/cm$^2$ of skin, decreased in fact the seriousness of the lesions caused by a local application of an hot water-device able to cause experimental burns of different degrees.

The intravenous injection in these animals of a vital dye such as Blue Evans, permitting to show the seriousness of the burn, showed that also the seriousness of the burn was not significantly different, in comparison with the control rats, in the rats treated only once half an hour before the induction of the burn, but it was reduced of more than 50% in the rats treated daily with Coenzyme $Q_{10}$ (1–2 mg/cm$^2$ of skin) for 4 consecutive days preceding the burn induction.

CARRAGEENIN OEDEMA TEST IN RATS

To male rats weighing 220 g, fasted for 24 hours, 0.1 ml of 1% carrageenin suspension was injected into the plantar surface of a hind paw.

The control group, consisting of 25 animals, was administered with the only carrageenin, two other groups, consisting each of 25 animals, were topically administered with Coenzyme $Q_{10}$ in form of two different formulations, in peanut oil and olive oil respectively, before the carrageenin injection. The results were expressed by means of a plethysmograph, which measured the size of the oedema 4 hours after the carrageenin injection.

The obtained results are set out in Table 4, which shows that the carrageenin oedema is partially inhibited in both groups of animals treated with Coenzyme $Q_{10}$.

TABLE 4

Percent inhibition versus controls of the carrageenin oedema in the rat paw, in animals treated with Coenzym $Q_{10}$ dissolved in peanut oil or soy oil and topically administered on the cutis.

| No animals (rats) | Treatment | Dosage | % Inhibition versus controls |
|---|---|---|---|
| 25 | Coenzyme $Q_{10}$ in peanut oil | 2 mg/cm$^2$ of cutis | 36 |
| 25 | Coenzyme $Q_{10}$ in soy oil | 2 mg/cm$^2$ of cutis | 40 |

TEST OF DITHRANOL INDUCED CUTANEOUS INFLAMMATION

Male Guinea pigs, weighing 330 g, were epilated at the back and, 24 hours after that, 20 mg of dithranol (anthralin) was intradermically injected into symmetric areas of the back.

Dithranol is a known inflammatory agent, which induces inflammatory response by releasing free radicals (Mustakallio K.K.—Dermatovener, 59-125, 1979).

Coenzyme $Q_{10}$ dissolved in peanut and soybean oil was spread on the backs of the animals under test, at the dosage of 2 mg/cm$^2$ cutis, whereas the control group of animals was subjected to no treatment.

The treated area was covered with Nescofilm and bound up with Micropore.

48 Hours after the administration of the inflammatory agent, the size of the induced inflammatory area was evaluated. The results are reported in Table 5, from which it appears that the inflammatory areas in the backs of the animals treated with Coenzyme $Q_{10}$ (both in peanut and soybean oil) showed a 50% decrease with respect to the non-treated ones.

TABLE 5

Percent inhibition versus controls of dithranol (anthralin) induced inflammatory reaction in the Guinea pig (cutis) by topical administration on the cutis of Coenzyme $Q_{10}$ dissolved in peanut oil or soy-bean oil

| No animals (Guinea pigs) | Treatment | Dosage | % Inhibiton with respect to controls of the inflammatory reaction |
|---|---|---|---|
| 10 | Coenzyme $Q_{10}$ in peanut oil | 2 mg/cm$^2$ of cutis | −52 |
| 10 | Coenzyme $Q_{10}$ in soy-bean oil | 2 mg/cm$^2$ of cutis | −57 |

What is claimed is:

1. A method of therapeutically treating impaired or damaged tissue in humans and animals which comprises topically administering to such tissue a composition comprising as the principal active ingredient a therapeutically effective amount of Coenzyme $Q_{10}$ (2,3-dimethoxy-5-methyl-6-decaprenyl-benzoquinone) in admixture with a pharmaceutically acceptable carrier.

2. A method according to claim 1 in which the amount of Coenzyme $Q_{10}$ in said composition is 0.1%–10% by weight.

3. A method according to claim 1 in which the amount of Coenzyme $Q_{10}$ in said composition is 0.0001–0.1% by weight.

4. A method according to claim 1 in which the pharmaceutically acceptable carrier is olive, peanut or soybean oil.

5. A method according to claim 1 in which the composition is in the form of a paste, cream, ointment, gel, lotion or unguent.

* * * * *